United States Patent [19]

Reaville et al.

[11] 4,097,994

[45] Jul. 4, 1978

[54] DENTAL RESTORATIVE COMPOSITION CONTAINING OLIGOMERIC BIS-GMA RESIN AND MICHLER'S KETONE

[75] Inventors: Eric T. Reaville, Webster Groves; Gudrun M. Streicher, St. Louis, both of Mo.

[73] Assignee: Monsanto Company, St. Louis, Mo.

[21] Appl. No.: 634,554

[22] Filed: Nov. 24, 1975

[51] Int. Cl.² .............................................. C08F 8/00
[52] U.S. Cl. .................................. 32/15; 204/159.16; 204/159.19; 204/159.23; 260/836; 260/837 R; 427/54; 428/413
[58] Field of Search ............... 204/159.19, 159.16, 204/159.23; 32/15; 260/836, 837 R

[56] References Cited

U.S. PATENT DOCUMENTS

| | | | |
|---|---|---|---|
| 3,673,140 | 6/1972 | Ackerman et al. | 260/22 TN |
| 3,709,866 | 1/1973 | Waller | 260/27 R |
| 3,713,864 | 1/1973 | Ackerman et al. | 117/38 |
| 3,772,171 | 11/1973 | Savageau et al. | 204/159.19 |

OTHER PUBLICATIONS

Buonocore, Adhesive Sealing for Caries Prevention, Journal of the American Dental Association, 80(2), 324–328 (1970).

*Primary Examiner*—Richard B. Turer
*Attorney, Agent, or Firm*—Scott J. Meyer; John D. Upham

[57] ABSTRACT

A dental restorative composition and tooth coating comprising the combination of an adhesive resin of the oligomeric BIS-GMA type, a low molecular weight reactive extender or diluent acrylate, an organic peroxide catalyst or free radical initiator and, as a photosensitizer, Michler's ketone.

8 Claims, 2 Drawing Figures

DENTAL RESTORATIVE COMPOSITION CONTAINING OLIGOMERIC BIS-GMA RESIN AND MICHLER'S KETONE

BACKGROUND OF THE INVENTION

This invention relates to a photo-polymerizable composition and, more particularly, to a rapidly photocurable resin composition useful for dental restorative and tooth coating purposes.

Adhesive compositions that harden when exposed to ultraviolet light have been used for dental restorative purposes for quite some time. In particular, various acrylic resins have been used as binders in these compositions. Compounds disclosed in U.S. Pat. Nos. 3,066,112, 3,179,623 and 3,194,784 are typical of these acrylic resins. Especially noteworthy is a compound having the formula

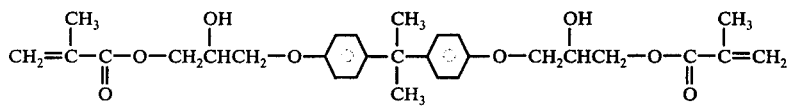

which is glycidyl methacrylate derivative of bisphenol-A, sometimes referred to as bisphenol-A-bis-(3-methacrylato-2-hydroxypropyl) ether or, more conveniently, as BIS-GMA.

The successful use of BIS-GMA in the adhesive sealing of pits and fissures for caries prevention with use of ultraviolet light has been described by Buonocore in *J. Amer. Dent. Assn.* 80 (2), 324–328 (1970). The major components of the adhesive composition were stated to be three parts by weight of the BIS-GMA and one part by weight of methyl methacrylate monomer. The adhesive, to which 2% benzoyl methyl ether was added just before used, was painted on acid-conditioned enamel surfaces and exposed to ultraviolet light for a few seconds to induce polymerization hardening.

In the foregoing BIS-GMA dental restorative compositions, the low molecular weight methyl methacrylte serves essentially as a reactive extender or diluent to reduce the viscosity of the compositions, as noted in U.S. Pat. Nos. 3,066,122, 3,539,533 and 3,709,866, whereby they can be conveniently used in dental applications. The benzoyl methyl ether is employed in these compositions as a photosensitizer. This is a substance which absorbs actinic radiation so as to produce free radicals which initiate polymerization and cross-linking reactions.

Another substance typically used in the dental restorative compositions is benzoyl peroxide or a similar such compound which serves as a free radical initiator or catalyst for the polymerization reaction.

While the foregoing dental restorative compositions are useful, a chronic problem which arises in practice is inhibition caused by the presence of oxygen. Because of this inhibition by oxygen, the desired complete hardening of the resin to the surface to which it is applied is not obtained and, instead, a tacky surface is produced.

BRIEF SUMMARY OF THE INVENTION

In accordance with the present invention, a rapidly photopolymerizable composition of the oligomeric BIS-GMA type suitable for dental restorative and tooth coating purposes is provided in which cure to a tack-free surface is obtained by the use of a particular ultraviolet sensitizer together with a peroxide catalyst. This sensitizer is the compound 4,4'-bis (dimethylamino) benzophenone, which also is known as Michler's ketone.

DETAILED DESCRIPTION OF THE INVENTION

In general, the photo-polymerizable composition of the present invention comprises the combination of an adhesive resin of the oligomeric BIS-GMA type, a low molecular weight reactive extender or diluent acrylate, a peroxide catalyst or free radical initiator and the aforementioned Michler's ketone.

While the specification concludes with claims particularly pointing out and distinctly claiming the subject matter regarded as forming the present invention, it is believed that the invention and its advantages will be better understood from the following description taken in connection with the accompanying drawings in which:

Figure 1:
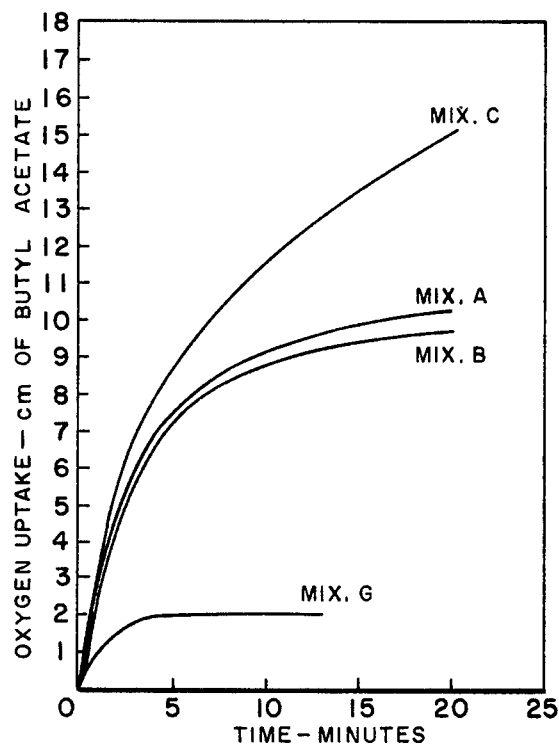
FIG. 1 is a series of curves showing the oxygen pickup with an exemplary composition of this invention when applied to a test surface and exposed to ultraviolet radiation.

Although the inventors are not bound by theory, it is believed that Michler's ketone on exposure to actinic radiation produces singlet oxygen which enters into the cross-linking reaction. However, because polymerization also takes place in the absence of oxygen, it is believed that another mechanism also is operative.

Thus, on exposure to actinic radiation, Michler's ketone absorbs a quantam of energy and becomes an excited state biradical. In the presence of oxygen, the energy of some of the excited state molecules is dissipated by transfer to ground state oxygen to produce an excited state species, probably the $^1\Delta g$ species. Other excited state molecules may transfer their energy to the peroxide catalyst, thereby cleaving it and initiating polymerization. In the absence of oxygen, the latter reaction is believed to be predominant. In the presence of oxygen, singlet oxygen may react with the tertiary nitrogens on Michler's ketone to produce species which enter into the cross-linking reaction. The type of products that singlet oxygen produces by reacting with tertiary nitrogen is disclosed, for example, by Gollnick and Lindner, *Tetrahedron Letters* 1903–1906 (1973).

Irrespective of its mechanism, it has been found that use of the Michler's ketone produces a rapid cure of the oligomeric BIS-GMA type resin. This rapid cure is obtained fully to the substrate surface. Michler's ketone is uniquely effective in the presence of oxygen and the composition containing it and can be applied in a thin coating, even less than 7 microns thick. By way of comparison, many other ketones, including the closely related benzophenone, 4,4'-dimethylbenzophenone, benzil, furil, thionil, xanthone, and anthraquinone are ineffective in the presence of oxygen. With certain other photosensitizers, such as thioxanthone and benzoyl ether, it is necessary to apply relatively thick coatings, thereby making it necessary to wipe off or abrade the uncured portion on the surface.

Although Michler's ketone has been disclosed heretofore as a photosensitizer in, for example, U.S. Pat. Nos. 3,597,216, 3,701,721 and 3,772,062, and numerous other patents, the present inventors are not aware of any previously suggested use in a dental restorative composition as defined herein. It was unexpected to find that Michler's ketone, as distinguished from other ultraviolet photosensitizers, has the aforesaid unique properties in dental restorative compositions.

The amount of Michler's ketone used in the dental restorative composition and tooth coating of this invention need be only a small but effective amount and generally ranges from about 0.25% to about 2% by weight of the total composition. For convenient usage, Michler's ketone can be incorporated in the dental restorative composition from admixture with a suitable solvent such as, for example, chloroform and the like organic solvents.

The oligomeric BIS-GMA type resin employed in the dental restorative composition of this invention can be conveniently represented by the following formula:

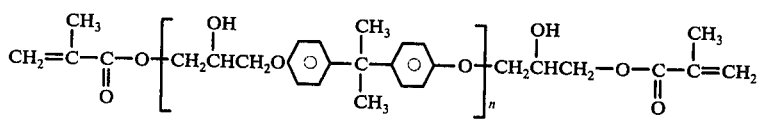

wherein $n$ ranges from about 1 to 10. Preferably, $n = 1$ to 5 and most preferably $n = 1$ to 3. Mixtures of these compounds can also be used, for example, a mixture of about equal parts of compounds in which $n = 1$ and $n = 3$.

The oligomeric BIS-GMA type resin can be prepared by well-known general methods. A preferred method involves first forming the polyepoxide and then esterifying the terminal groups. Thus, at least about 2 moles of epihalohydrin can be reacted with about one mole of propylidene diphenol and a sufficient amount of alkali to combine with the halogen of the epihalohydrin to form the polyepoxide which includes structures represented by the following formula:

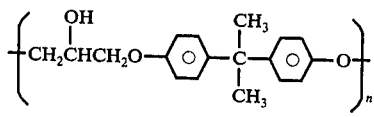

The chain thus formed may be terminated at one or both ends by an epoxy group

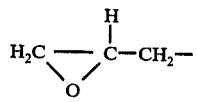

or a hydroxyl. Methacrylic acid is then reacted with the polyepoxide at the terminal groups to form the desired oligomeric BIS-GMA type resin.

The reactive extender or diluent acrylate used in the present invention is a relatively low molecular weight, low viscosity, aliphatic methacrylate monomer such as, for example, methyl methacrylate, ethyl methacrylate, n-propyl methacrylate, iso-propyl methacrylate, n-butyl methacrylate, iso-butyl methacrylate, sec-butyl methacrylate, tert-butyl methacrylate, the amyl methacrylates, ethylene dimethacrylate, butylene dimethacrylate, ethylene glycol monomethacrylate, ethylene glycol dimethacrylate, triethylene glycol dimethacrylate and tetraethylene glycol dimethacrylate. These diluents are used in amounts sufficient to lower the viscosity and make the oligomeric BIS-GMA resin composition pourable at ordinary room temperatures such as at about 20°-25° C. Generally, use of from about 30% to about 80% by weight of the oligomeric BIS-GMA polymer with from about 70% to about 20% by weight of the diluent acrylate is suitable and use of about equal parts by weight of the oligomeric BIS-GMA and the diluent acrylate is preferred.

As the peroxide catalyst or free radical initiator for use in the present invention, any of the known organic peroxides are suitable such as, for example, benzoyl peroxide, phthaloyl peroxide, napthoyl peroxide, alkyl- or alkanoyl- substituted peroxides such as acetyl, caproyl, lauroyl, tertiary butyl and di-t-butyl peroxides, alkyl-, alkanoyl- or chloro-substituted benzoyl peroxides such as acetyl benzoyl peroxide, dimethyl benzoyl peroxide and 2,4-dichloro-benzoyl peroxide, hydroperoxides such as di-isopropyl-benzene hydroperoxide, t-butyl hydroperoxide, and cumene hydroperoxide, and still other peroxides such as cinnamoyl peroxide, methyl ethyl ketone peroxide and urea peroxide.

Only minor amounts of the peroxide initiators are required and generally from about 0.5% to about 2% by weight of the total composition is suitable.

It will be appreciated that various other substances can also be employed in the dental resin composition of this invention provided that they do not interfere with the basic and novel effects of the required components as defined herein. Thus, small amounts of pigments such as, for example, the fluorescent pigments described in U.S. Pat. No. 2,481,344 can be used in the composition, if desired. Inert fillers such as finely divided crystalline quartz, fused silica, aluminum oxide, lithium aluminum silicate and the like inorganic minerals and vitreous particulate fillers such as disclosed in U.S. Pat. Nos. 3,066,112 and 3,503,128 can be incorporated in the dental resin composition to the extent desired.

Application of the aforesaid composition for dental restorative and tooth coating purposes can be made by conventional techniques such as by brushing, spraying or dipping to give a thin film such as 5 to 100 microns, on a tooth or dental support which is then exposed to actinic radiation for a few seconds. Thus, exposure to long wave ultraviolet light of flux of about $10^5$ ergs/cm$^2$/sec for about 15 to 30 seconds is eminently satisfactory.

In practice, the composition of this invention can be packaged in kit form suitable for distribution to dentists and dental supply houses. For this purpose and in order to promote shelf stability, it is desirable to divide the components into at least two parts in which the organic peroxide free radical initiator is separate from the oligomeric BIS-GMA type resin. In this kit form, the diluent acrylate and Michler's ketone can be conveniently placed in admixture with the resin in one container and the benzoyl peroxide can be conveniently put into admixture with an organic solvent in a second container to thereby reduce the number of containers used. Prior to use, the dentist or dental technician can readily combine the contents of the two containers to thereby render the complete composition into an admixture suitable for application to teeth.

An illustrative example of such a kit form of the composition of the present invention comprises a two-package kit of solutions A and B. Solution A can comprise, for example, 48.0 grams of the oligomeric BIS-GMA type resin, 51.3 grams of methyl methacrylate and 0.7 grams of Michler's ketone. Solution B can comprise, for example, 16 grams of benzoyl peroxide in 84 grams of chloroform or similar such solvent. Prior to use, one part of solution B can be admixed with eight parts of solution A and the mixture then applied to teeth. Other examples of the preparation of the composition in kit form will be apparent to the person skilled in the art.

The following examples will further illustrate the invention although it should be understood that the invention is not limited to these examples. In these examples, the oligomeric BIS-GMA used was Dow Resin XD 3586.00.

EXAMPLE 1

A pourable resin mixture is made by thinning 66.7 parts by weight of oligomeric BIS-GMA with 33.3 parts by weight of methyl methacrylate. To this mixture is added 40 parts by weight of a 5% by weight solution of benzoyl peroxide in methyl methacrylate and 20 parts by weight of a 5% by weight solution of 4,4'-bis-(dimethylamino) benzophenone dissolved in chloroform. The components are thoroughly mixed and then applied by brushing, spraying and dipping to give a thin film, 5 to 100 microns, on a support which when exposed to long wave ultraviolet light of a flux about $10^5$ ergs/cm$^2$/sec becomes tack free in fifteen to thirty seconds.

EXAMPLE 2

Three pourable resin mixtures are made by thinning 66.7 parts by weight of oligomeric BIS-GMA with 33.3 parts by weight of, respectively, (a) methyl methacrylate, (b) ethyl methacrylate, and (c) n-propyl methacrylate. Into each mixture is then dissolved one part by weight of 4,4'-bis(dimethylamino) benzophenone. To each mixture is added 40 parts by weight of a 5% solution of benzoyl peroxide dissolved in methyl methacrylate. The mixtures are applied by brushing, spraying and dipping to acid-etched, extracted human teeth in film thickness of 5 to 100 microns. On exposure to long wave ultraviolet light of flux of $10^5$ ergs/cm$^2$/sec, the surfaces become tack-free in about fifteen to thirty seconds.

The Knoop hardness of the foregoing films is about 22. The Knoop hardness is measured by the length of an indenture produced by a pyramidyl shaped diamond under a load in accordance with the standard test described in *The Journal of Research, National Bureau of Standards* 23, 39 (1939).

By contrast, Nuva Seal ®, a commercially available dental pit and fissure sealant*, did not become tack-free on similar treatment after 10 minutes exposure to ultraviolet light. Excess material had to be removed by rubbing with a wet cotton ball, which left a rough surface of a substantially lower Knoop hardness of about 11.

*Contains BIS-GMA and methyl methacrylate formulation disclosed in *J. Amer. Dent. Assn.* 80(2), 324–8 (1970).

EXAMPLE 3

In order to demonstrate the excellent oxygen pick-up of the dental restorative composition of this invention, the following tests were carried out in which the aforementioned dental pit and fissure sealant sold under the trademark Nuva Seal ® was used as a standard for comparison.

Mixture A

A mixture was made as follows:

| Component | Percent by Weight |
| --- | --- |
| Oligomeric BIS-GMA | 47.3 |
| Methyl methacrylate | 50.6 |
| Benzoyl peroxide | 1.4 |
| Michler's ketone | 0.7 |
|  | 100.0% |

Mixture B

A portion of Mixture A was diluted with 0.2 gram hexadecanol per gram of Mixture A to form Mixture B.

Mixture C

A portion of Mixture A was diluted with 0.2 gram squalene per gram of Mixture A to form Mixture C.

Mixture D

This mixture consisted of undiluted Nuva Seal ® dental pit and fissure sealant.

Mixture E

A portion of Mixture D was diluted with 0.4 gram methyl methacrylate and 0.2 gram hexadecanol per gram of Mixture D to form Mixture E.

Mixture F

A portion of Mixture D was diluted with 0.4 gram methyl methacrylate and 0.2 gram squalene per gram of Mixture D to form Mixture F.

In the foregoing mixtures, hexadecanol was used as a common solvent to vary the consistency of the compositions being tested and squalene was used as a well-known singlet oxygen acceptor. In Mixtures E and F, methyl methacrylate was used as a reactive diluent to provide a viscosity equivalent to that of Mixtures B and C, respectively.

Samples of the foregoing resin mixtures were each drawn with a wire wound rod on a sheet of release paper, Transkote ER ®, about 3 inches × 4 inches in size, allowed to stand five minutes in air and then inserted in an opening of a Teflon ® plastic gasket. The gasket was about ⅛ inch thick and had an opening size of about 4 inches × 5 inches. On the top and bottom sides of the gasket, clear glass plates were clamped to effectively seal the sheet from the atmosphere. A connection on the bottom plate led from the opening in the gasket to a fine bore capillary, used as a manometer, which was filled with butyl acetate. Upon irradiation of the resin mixtures through the top plate by ultraviolet light, flux of about 4 × $10^3$ ergs/cm$^2$/sec, the uptake of oxygen was measured by the drop in the manometer fluid.

Figure 2:
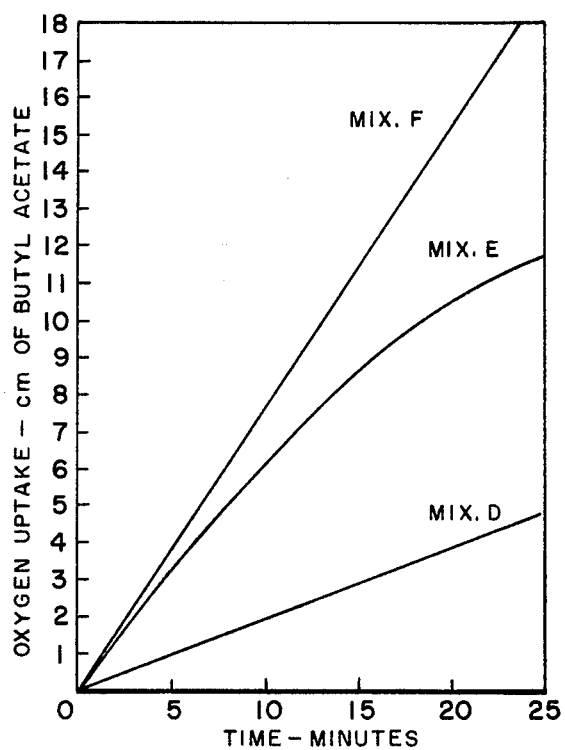
FIG. 2 is a series of curves showing the oxygen pickup with a standard commercially available dental pit and fissure sealant when applied to a test surface and exposed to ultraviolet radiation.

FIG. 1 of the drawings shows the uptake of oxygen with Mixtures A, B, and C (Curves Mix. A, B and C) whereas FIG. 2 shows the oxygen uptake with Mixtures D, E and F (Curves Mix. D, E, and F). In the curves shown in these figures, the oxygen uptake in centimeters of butyl acetate is plotted against time in minutes following the onset of exposure to ultraviolet radiation.

All of Mixtures A through F were drawn with a standard #24 wire wound rod to give a final film thickness of about 22 microns. FIG. 1 shows an additional curve G in which Mixture A was drawn with a #8 wire wound rod to yield a final film thickness of about 7 microns.

The results demonstrate the excellent rapid oxygen pick-up of the composition of the present invention when compared with the commercially available Nuva Seal®. The total oxygen pick-up also was substantially better with Mixtures A, B and C as evident by the amounts shown in the critical early part of the time curve. In addition, all of the films formed by Mixtures A, B and C were tack-free whereas the films produced by Mixtures D, E and F were tacky.

Various other examples will be apparent to the person skilled in the art after reading the foregoing description without departing from the spirit and scope of the invention. All such further examples are included within the scope of the claims as appended hereto.

What is claimed is:

1. A photo-polymerizable composition suitable for dental restorative and tooth coating purposes comprising from about 30% to about 80% by weight of oligomeric resin having the formula

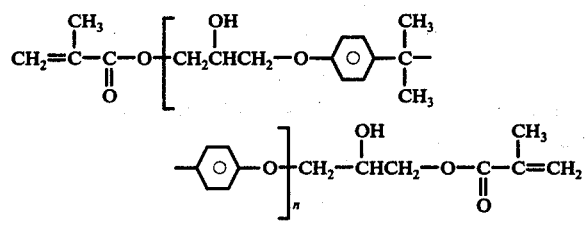

wherein $n$ ranges from about 1 to 10, and mixtures thereof, from about 70% to about 20% by weight low molecular weight low viscosity diluent aliphatic acrylate monomer, from about 0.5% to about 2% by weight organic peroxide free radical initiator and from about 0.25% to about 2% by weight photosensitizer comprising 4,4'-bis(dimethylamino)benzophenone.

2. The composition of claim 1 in which $n$ ranges from about 1 to 5.

3. The composition of claim 1 in which the diluent acrylate is methyl methacrylate.

4. The composition of claim 1 in which the organic peroxide is benzoyl peroxide.

5. The composition of claim 1 in which $n$ ranges from about 1 to 5, the diluent acrylate is methyl methacrylate and the organic peroxide is benzoyl peroxide.

6. The composition of claim 1 in kit form suitable for use by admixture thereof in which the organic peroxide is packaged in a container separate from the oligomeric resin.

7. In the preparation of a photopolymerizable composition suitable for dental restorative and tooth coating purposes comprising a polymerizable acrylate resin, a low molecular weight low viscosity diluent aliphatic acrylate monomer, an organic peroxide free radical initiator and a photosensitizer, the improvement comprising providing as the polymerizable acrylate resin an oligomeric resin having the formula

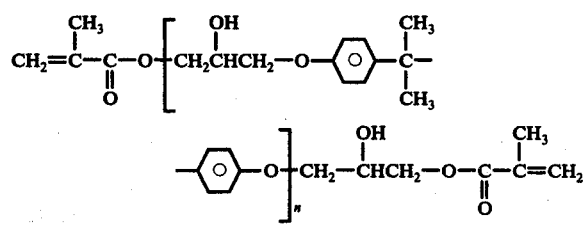

wherein $n$ ranges from about 1 to 10, and mixtures thereof, and providing as the photosensitizer the compound 4,4'-bis-(dimethylamino)benzophenone, all said components being present in the relative amounts set forth in claim 1.

8. The method of treating teeth for restorative or coating purposes in the presence of oxygen comprising contacting said teeth with the composition of claim 1 and allowing said composition to cure to an essentially tack-free surface.

* * * * *